US00PP12762P2

(12) United States Plant Patent
Olesen et al.

(10) Patent No.: US PP12,762 P2
(45) Date of Patent: Jul. 9, 2002

(54) MINIATURE ROSE VARIETY 'POULHILDA'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 20 days.

(21) Appl. No.: 09/607,330

(22) Filed: Jun. 30, 2000

(51) Int. Cl.[7] ..... A01H 5/00
(52) U.S. Cl. ..... Plt./117
(58) Field of Search ..... Plt./117

(56) References Cited

PUBLICATIONS

UPOV–ROM GTITM Computer Database, 2001/02, GTI Jouve Retrieval Software, citation for 'POULhilda'.*
Community Plant Variety Office "Certificate on the Grant . . . " Aug. 3, 1998 EU 6 pages.
Community Plant Variety Office "Proposal For A Variety Denomination" Jan. 27, 1997 1 page EU.
Community Plant Variety Office "Chapter IV: Decisions" 2 pages Oct. 15, 1998 EU.
Canadian Food Inspection Agency "Applications Accepted for Filing" Jan. 1999 Canada 1 page.

* cited by examiner

*Primary Examiner*—Bruce R. Campell
*Assistant Examiner*—Susan B. McCormick

(57) ABSTRACT

A new miniature rose plant which has abundant, light pink flowers and attractive foliage. The variety successfully propagates from softwood cuttings and is suitable for year round production in commercial glasshouses. This new and distinct variety has shown to be uniform and stable in the resulting generations from asexual propagation.

2 Drawing Sheets

SUMMARY OF THE INVENTION

The present invention constitutes a new and distinct variety of miniature rose plant which originated from a controlled crossing between 'POULvic' (U.S. Plant Pat. No. 8,012, issued on Oct. 27, 1994) and an unnamed seedling. The two parents were crossed and the resulting seeds were planted in a controlled environment. The new variety is named 'POULhilda'.

The new rose may be distinguished from its seed parent, 'POULvic', by the following combination of characteristics:

1. The color of 'POULvic''s flower is orange-red, where that of 'POULhilda' is light pink.
2. The flowers of 'POULvic' are smaller than those of 'POULhilda'.
3. The growth habit of 'POULvic' is lower than that of 'POULhilda'.
4. The foliage of 'POULvic' is smaller than that of 'POULhilda'.

The new variety may be distinguished from its pollen parent, an unnamed seedling, by the following combination of characteristics:

1. The flower of the unnamed pollen parent is white, where that of 'POULhilda' is light pink.
2. The growth habit of the unnamed pollen parent is more vigorous than that of 'POULhilda'.

The objective of the hybridization of this rose variety for commercial greenhouse culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type and distinguish 'POULhilda' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhilda' was selected by the inventors as a single plant from the progeny of the hybridization in Fredensborg, Denmark in July of 1995.

Asexual reproduction of 'POULhilda' by cuttings and traditional budding was first done by L. Pernille and Mogens N. Olesen in Fredensborg, Denmark. This initial and other subsequent propagations conducted in controlled environments have demonstrated that the characteristics of 'POULhilda' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULhilda'. Specifically illustrated in SHEET 1:

1. Stem or entire plant showing branching and the attachment of leaves, buds, and peduncles;
2. Flower bud, partially opened bud, and open bloom;
3. Flower petals, detached;

Specifically illustrated in Sheet 2:

4. Sepals, receptacle, and pedicel;

5. Flowering stem as well as a bare stem exhibiting thorns;
6. Leaves.

DETAILED DESCRIPTION OF THE VARIETY

The following is a description of 'POULhilda', as observed in its growth in glasshouses in Half Moon Bay, Calif. in plants aged sixteen weeks. Color references are made using The Royal Horticultural Society (London, England) Colour Chart, 1995, except where common terms of color are used.

For a comparison, several physical characteristics of the rose variety 'POULavon', a miniature rose variety from the same inventors described and illustrated in U.S. Plant Pat. No. 10,082 and issued on Oct. 28, 1997 are compared to 'POULhilda' in Chart 1.

CHART 1

| | 'POULhilda' | 'POULavon' |
|---|---|---|
| Petal color after opening: upper surface. | Red Group 49C in marginal zone, White Group 155D in middle and basal zones. | Red Group 36D |
| Petal count: | 95 to 100 Petals. | 30 to 35 Petals. |
| Bloom size: | Large: 48 to 52 mm. | Small: 38 to 45 mm. |

Parents: 'POULvic'×Unnamed Seedling.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 18 to 20 mm in length from base of receptacle to end of bud.
*Bud form.*—Bud color: As sepals unfold, Red Group 49D. Red Group 49C at ¼ opening. Sepals: Sepals are 18 to 22 mm long and 10 mm wide. Green Group 137C. Weak foliaceous appendages on three of the five sepals. Surfaces of sepals moderately pubescent. Stipitate glands are present on margins. Tiny, white hairs present on upper surface of sepal.
*Receptacle.*—Surface: Smooth, with scant fine, white hairs. Shape: Urn-shaped. Size: 3 to 4 mm (h)×5 to 7 mm (w). Color: Yellow-Green Group 144A.
*Peduncle.*—Surface: Smooth, with scant fine, white hairs. Length: 40 to 50 mm average length. Color: Yellow-Green Group 144A. Strength: Strong.
*Borne.*—Generally with 2 to 3 buds per flowering stem.
Flower bloom:
*Fragrance.*—Light floral scent.
*Duration.*—As a pot plant, flowers last from 8 to 12 days. As a cut flower 3 to 4 days.
*Size.*—Large for a 12 cm pot rose. Average flower diameter is 48 to 52 mm when open.
*Form.*—Shape of flower when viewed from the side: Upon opening, upper part: Flat. Upon opening, lower part: Flattened convex. Open flower, upper part: Flattened convex. Open flower, lower part: Flat.
*Petalage.*—Average range: 95 to 100 petals under normal conditions with 10 to 12 petaloids.
Color:
*Upon opening, petals.*—Outermost petals: Upper Surface: Red Group 49D in marginal zone, White Group 155D in middle and basal zones. Reverse Side: Red Group 49D in marginal zone, White Group 155D in middle and basal zones. Innermost petals: Upper Surface: Red Group 49D in marginal zone, White Group 155D in middle and basal zones. Reverse Side: Red Group 49D in marginal zone, White Group 155D in middle and basal zones.
*Upon opening, basal petal spots.*—Outermost petals: Outer Side: Green-White Group 157A. Inner Side: Green-White Group 157A. Innermost petals: Outer Side: Green-White Group 157A. Inner Side: Green-White Group 157A.
*After opening, petals.*—Outermost petals: Upper Surface: Green-White Group 157A in basal and middle zones, Red Group 49C and D in marginal zone. Reverse Side: Green-White Group 157A in basal and middle zones, Red Group 49C and D in marginal zone. Innermost petals: Upper Surface: Green-White Group 157A in basal and middle zones, Red Group 49C and D in marginal zone. Reverse Side: Green-White Group 157A in basal and middle zones, Red Group 49C and D in marginal zone.
*Upon opening, basal petal spots: No distinctive coloration at petal base observed.*—Outermost petals: Outer Side: Green-White Group 157A. Inner Side: Green-White Group 157A. Innermost petals: Outer Side: Green-White Group 157A. Inner Side: Green-White Group 157A.
General tonality: On open flower Red Group 49 C and D. No change in the general tonality at the end of the third day. Afterwards, general tonality is Red Group 49D.
Petals:
*Petal reflex.*—Outermost petals double reflexed. Inner petals reflexed.
*Petal margins.*—Petal margins have point in center.
*Shape.*—Rounded deltoid.
*Petaloids.*—8 to 12.
*Thickness.*—Average.
*Arrangement.*—Imbricated.
Reproductive organs:
*Pollen.*—Color: Greyed-Orange Group 166B and C. Quantity: Scant.
*Anthers.*—Size: 1–2 mm long. Color: Yellow-Orange Group 17 B and C. Quantity: 25 to 30. Length: 2 mm.
*Filaments.*—Color: Yellow-Green Group 149D.
*Stigmas.*—Stigmas are significantly superior to anthers. Color: Yellow-Green Group 149C. Quantity: 20 to 25.
*Styles.*—Color: Yellow-Green Group 149C, fading to Yellow-Green Group 149D. Length: 5 mm.

PLANT

Plant growth: Vigorous, compact, upright to bushy. When grown as a 10 cm pot plant, the average height of the plant itself is 26 cm and the average width is 21 to 23 cm. When grown as a budded field grown plant on multiflora understock, the average height of the plant itself is 39 cm and the average width is 32 to 35 cm.
Stems:
*Color.*—Young wood: Yellow-Green Group 144A. Older wood: Yellow-Green Group 144A.
*Thorns.*—Incidence: Moderate. Size: Average length: 3 mm. Color: Greyed-Red Group 181C. Shape: Linear.
*Surface.*—Young wood: Smooth. Older wood: Smooth. Length: Under typical greenhouse production conditions, stem length is 40 to 50 cm. Internode length varies from 10 to 12 cm.

Plant foliage: Typical number of leaflets on leaves in middle of the stem: 5 leaflets.

*Leaf size.*—92 mm (l)×65 mm (w).

*Abundance.*—Average.

*Color.*—Upper Leaf Surface: Green Group 139A. Lower Leaf Surface: Green Group 139B. Juvenile foliage: Green Group 137A on upper surface, Yellow-Green Group 146B. Anthocyanin intonation: Location: Leaflet margins, young thorns, and stipules. Color: Greyed-Red Group 182B.

Plant leaves and leaflets:

*Stipules.*—Size: 8 to 10 mm. Color: Yellow-Green Group 144A. Stipitate glands: Present on margins.

*Petiole.*—Length: 25 mm. Color: Green Group 137A. Underneath: Green Group 137A. One to two prickles present.

*Rachis.*—Color: Green Group 137A. Underneath: Green Group 143A. One to two prickles present.

*Leaflet.*—Edge: Serrated. Shape: Ovate. Texture: Thick, with semi-glossy finish.

Disease resistance: Average resistance to mildew, black spot, and Botrytis under normal growing conditions in Half Moon Bay, Calif., Jackson County, Oreg., Burlington, Canada, and Fredensborg, Denmark.

Cold hardiness: 'POULhilda' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, light pink flowers, vigorous and compact growth, year round flowering under glasshouse conditions, suitability for production from softwood cuttings in pots, and durable flowers and foliage which make the variety suitable for distribution in the floral industry.

* * * * *

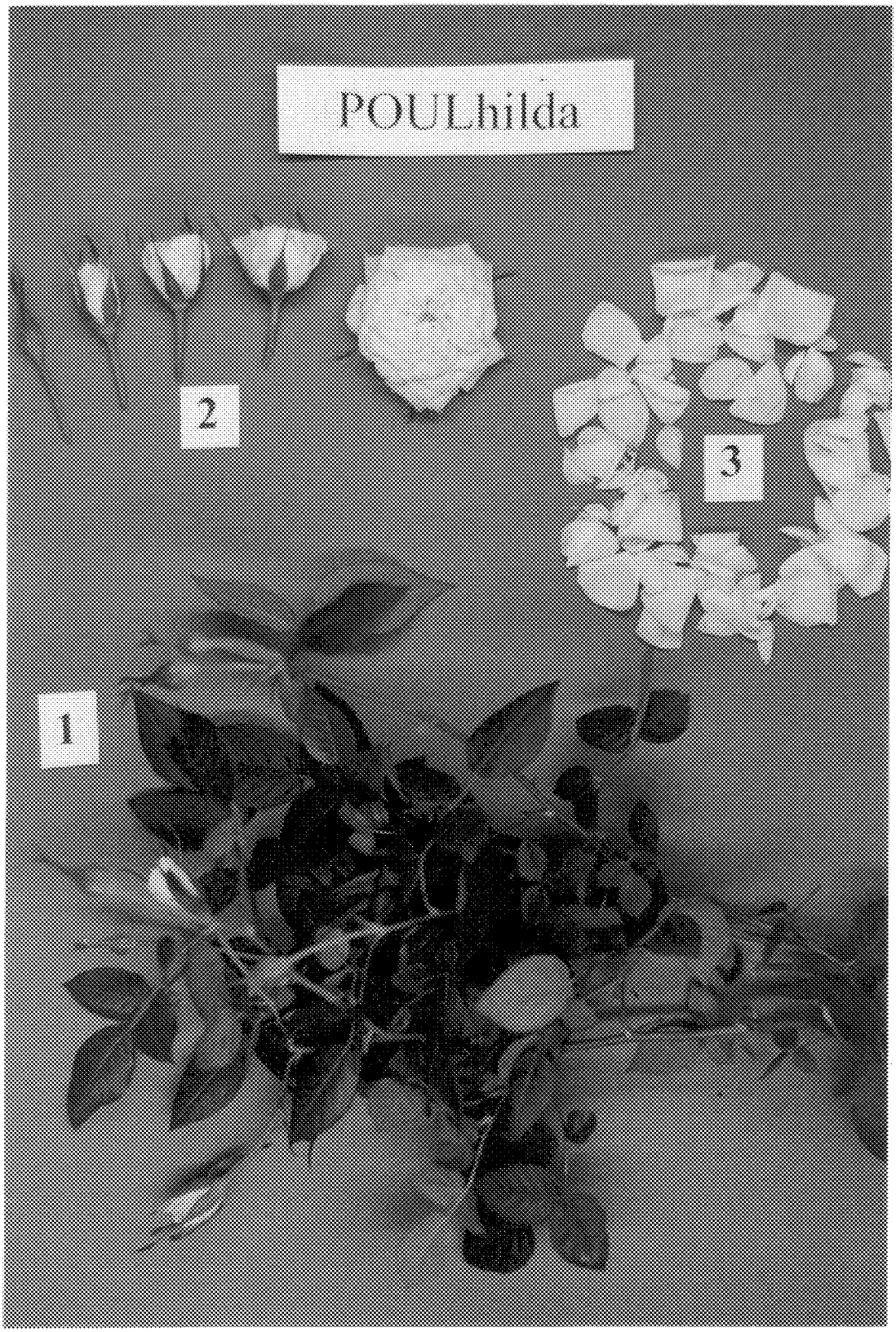
POULhilda
2
3
1

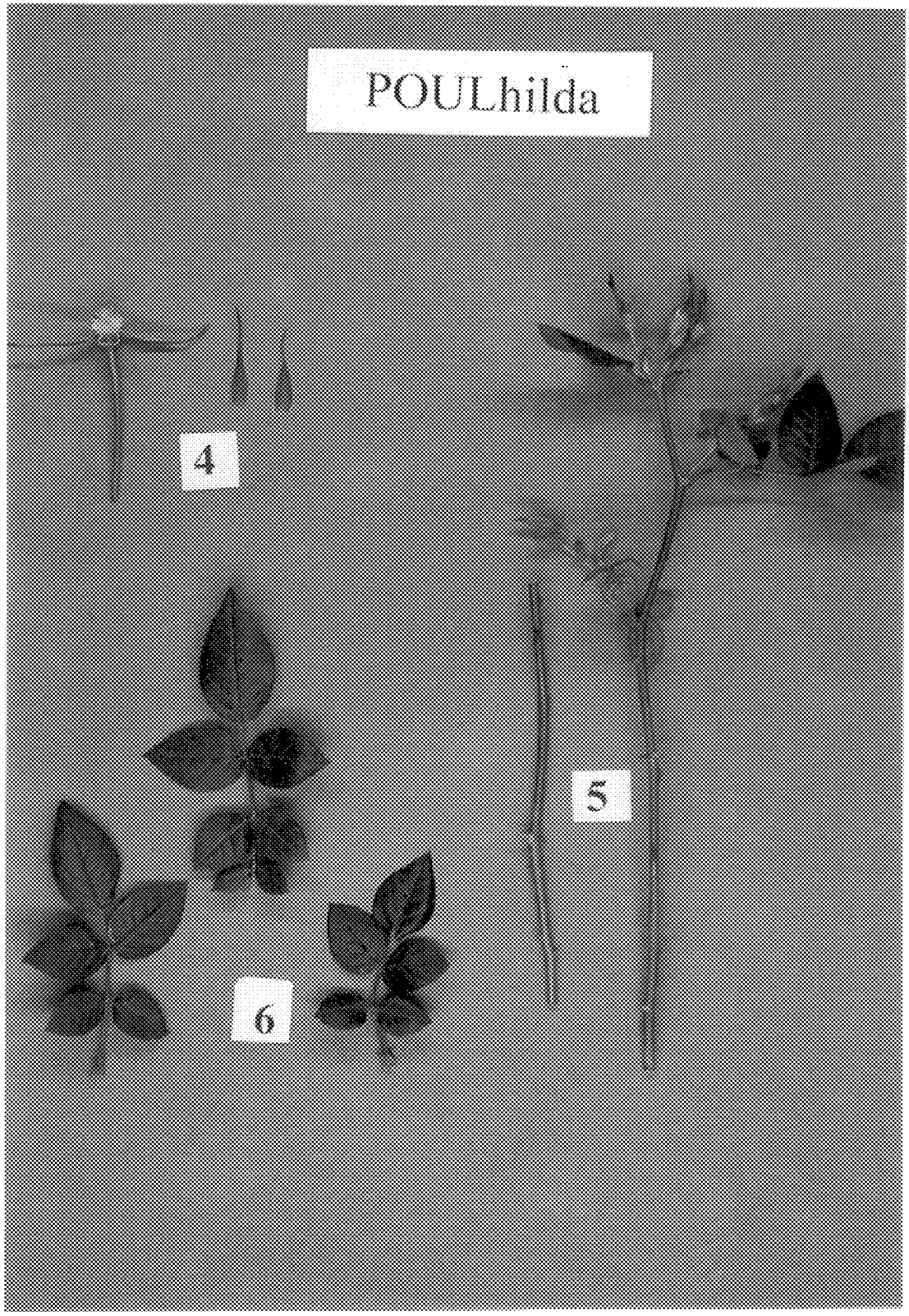
POULhilda
4
5
6